: 
United States Patent [19]

Barreras, Sr. et al.

[11] Patent Number: 5,941,906
[45] Date of Patent: Aug. 24, 1999

[54] IMPLANTABLE, MODULAR TISSUE STIMULATOR

[75] Inventors: Francisco J. Barreras, Sr.; Roberto Echarri; Guillermo Echarri, all of Miami, Fla.

[73] Assignee: Medtronic, Inc., Minneapolis, Minn.

[21] Appl. No.: 08/950,932

[22] Filed: Oct. 15, 1997

[51] Int. Cl.[6] .................................................. A61N 1/36
[52] U.S. Cl. .............................................. 607/66; 607/60
[58] Field of Search ................................ 607/66, 67, 68, 607/72, 60

[56] References Cited

U.S. PATENT DOCUMENTS

| | | | |
|---|---|---|---|
| 4,841,973 | 6/1989 | Stecker ........................................ | 607/66 |
| 5,501,703 | 3/1996 | Holsheimer et al. . | |
| 5,630,836 | 5/1997 | Prem et al. ................................. | 607/61 |
| 5,643,330 | 7/1997 | Holsheimer et al. . | |

*Primary Examiner*—Scott M. Getzow
*Attorney, Agent, or Firm*—Thomas R. Vigil

[57] ABSTRACT

The implantable, electrically operated tissue stimulator system comprises a master controller module having a microcontroller, a telemetry circuit, a power module, non-volatile memory, a real time clock and a bi-directional bus, and a plurality of Input/Output modules (I/O modules) which are connected to said bi-directional bus. Each I/O module 16 comprises (1) a control logic, (2) a programmable DC/DC Converter, (3) a capacitor multiplexer, (4) two or more electrodes (channels), (5) one amplitude holding capacitor per electrode, including circuitry for isolating the holding capacitor from other holding capacitors, and a switching network used for isolating the main power source from the electrodes during delivery of the stimulation pulses. Each I/O module can be used to (I) deliver stimulus pulses to two or more preselected channels, each channel being capable of being programmed to deliver pulses having a different amplitude, pulse width and rate, and each channel being capable of being programmed to stimulate either, in isolation from other channels or in combination with other channels, (II) learn and record into non-volatile memory the morphology of a biological signal, compare the prerecorded morphology against that of freshly acquired signals, and, upon a positive comparison, respond by either, initiating or terminating a preselected stimulation schedule, modifying the on-going stimulation schedule, or up-linking a command to another external medical device to initiate delivery of medical therapy, (III) write into non-volatile memory the time and date when adjustments are made to any of the stimulation parameters along with the new stimulation value (adjustments data base), and (IV) on a periodic basis or upon command, measure and write into non-volatile memory electrode impedance values along with the time and date when the adjustments are made (impedance data base).

44 Claims, 13 Drawing Sheets

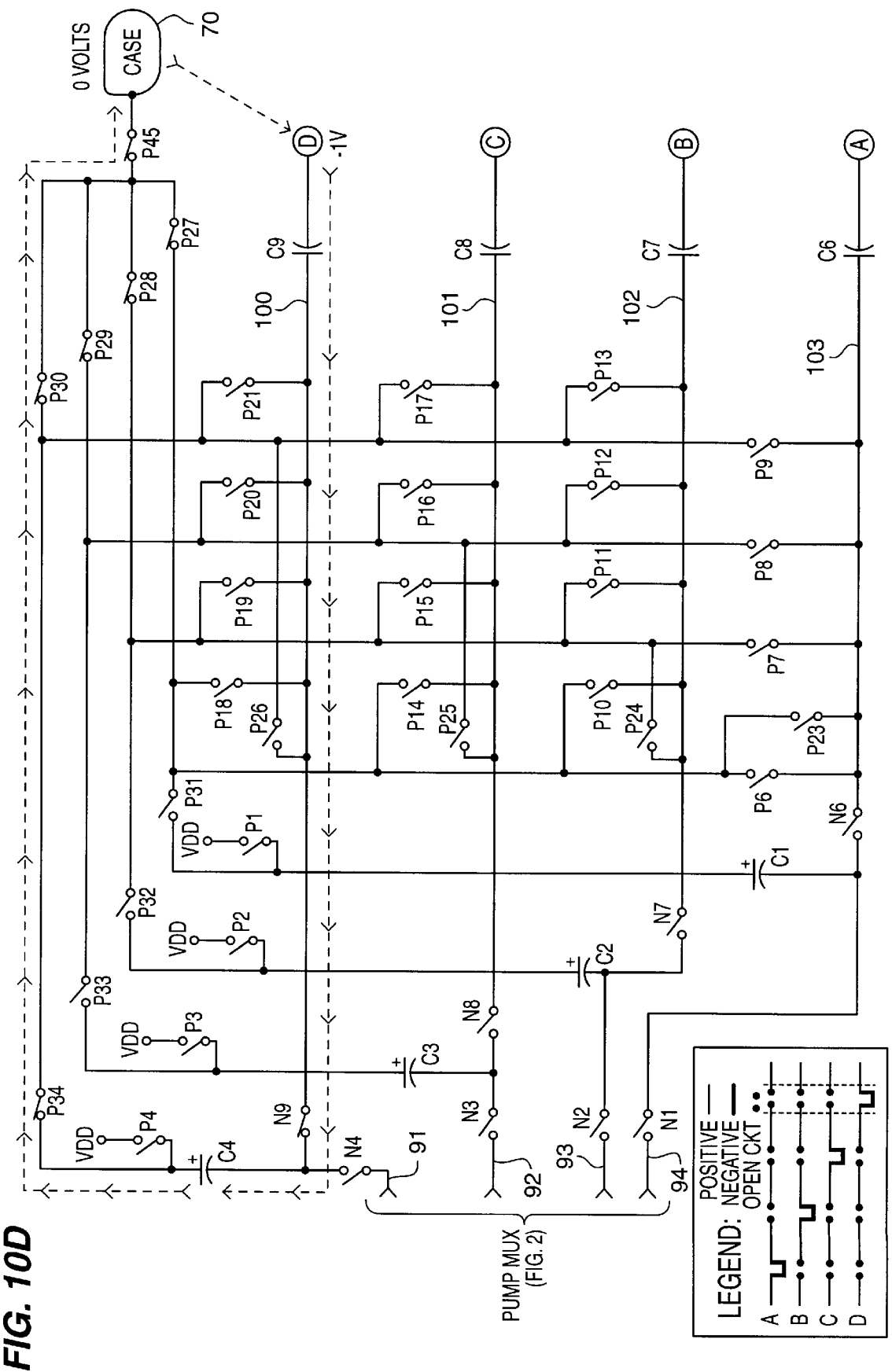

IMPLANTABLE, MODULAR TISSUE STIMULATOR

BACKGROUND OF THE INVENTION

1. Field of the Invention

The present invention relates to an implantable, modular tissue stimulator comprising (a) a master controller including a micro-controller, non-volatile memory, circuitry for receiving signals down-linked by external devices representing commands or program data and circuitry for up-linking signals representing stored data or commands to external devices; (b) two or more I/O modules each having two or more stimulating electrodes, circuitry for delivering electrical pulses of different amplitude, pulse width and rate to each electrode, and circuitry for powering the circuitry driving each electrode from an isolated power source; and, (c) a bidirectional bus carrying data and controlling signals between the master controller and the I/O modules.

2. Description of the Prior Art

The concept of using implantable, electrically operated tissue stimulators for treating specific diseases or physical disorders is well known. Some examples are cardiac pacemakers which restore a sick human heart to a normal rhythm, neural stimulators which control nerve or brain response (such as pain or epileptic seizures), and cardioverter defibrillators which, upon sensing a fibrillation episode, automatically delivers an electric shock to the heart to restore a normal rhythm.

The use of implantable, electrically operated neural stimulator systems has been well established for a number of years, especially for the control of nerve or brain response to treat intractable pain, epileptic seizures and tremors as a result of Parkinson disease.

An example of a prior art neural stimulator system is an RF coupled device comprising an external RF transmitter and a surgically implanted receiver whereby RF energy is coupled into the receiver to power the neural stimulator. The RF transmitter generates a radio frequency carrier which is modulated twice for each stimulus pulse, first to designate to the receiver which electrodes are to be used to deliver the stimulus pulse and their respective polarity, and secondly, the amplitude of the carrier is modulated for a period corresponding to the stimulus pulse width, the peak modulated voltage representing the pulse amplitude.

The amplitude of the stimulation pulse delivered by the receiver is proportional to the peak value of the RF signal received during the stimulation portion of the carrier wave form. The frequency of stimulation is controlled by the RF transmitter by simply adjusting the repetition rate of the modulation.

For some clinical indications, electrical isolation between separate stimulation channels is required so that when one channel delivers a stimulus pulse the current flow is confined to the active electrodes within that channel and do not traverse to electrodes in another channel.

For example, electrical isolation may be required for treating patients feeling pain in more than one area of their bodies. Such patients benefit from a single implanted stimulator having two or more channels, each channel delivering a different stimulation schedule, and each schedule being designed to provide pain relief in a specific area of the patient's body.

However, there are other clinical applications in which current traversing between electrodes in different channels is desirable, such as when trying to recruit specific nerve fibers by forming current vectors between two or more stimulation channels whereby the resulting electric field can be steered and focused with greater precision than is otherwise possible with a single stimulation channel.

In summary, it is a desirable option to be able to non-invasively program the device to stimulate in "isolation" mode when the electric current needs to be confined to pre-selected electrodes within the channel generating said current, or alternatively in "combination" mode when a steerable electric field is required to achieve effective therapy.

RF coupled neuro modulation systems are easily configured to multiple channels where each channel must be programmed to a different amplitude than other channel(s) but with electrical isolation between the two channels. Since inductors are employed in the implanted RF stimulator to gather the RF energy which powers the stimulator, one receiving inductor per channel can be used to provide an independent power supply for each channel in order to achieve total isolation between channels. Furthermore, independent frequency and pulse width can be achieved easily in the RF coupled stimulator by simply alternatively modulating the carrier at two (or more) different frequencies, each frequency value designating the pulse width and rate for a particular channel.

In the case of a self-powered stimulator employing a single battery as the power source, it is much more difficult to design a multiple channel stimulator with total isolation between channels, when each channel stimulates at a different amplitude, pulse width and rate. For reasons of volumetric efficiency and manufacturing cost, it is impractical to design a multichannel, self-powered stimulator employing several batteries (one for each channel) in order to achieve the necessary isolation. Furthermore, if one battery per channel were used, the resulting stimulation system would only operate in the "isolation" mode and the "combination" option would not be available.

Another deficiency often encountered with prior art neural stimulators, is that constant voltage pulses are used to stimulate nerve tissue. In a constant voltage stimulation the voltage amplitude remains unchanged as the impedance at the electrode/tissue interface varies. If a multiple channel neural stimulator generating constant voltage pulses is employed in the "combination" mode to steer and focus the electric field to recruit specific nerve tissue, the location of the electric field will migrate as a result of the impedance variations, resulting in inefficient therapy.

Another deficiency often encountered with prior art neural stimulators, is that delivered amplitude varies as a function of stimulation pulse width and electrode impedance, due to losses in the transistors used to deliver the stimulation pulses to the electrodes. Pulse amplitude is probably the most critical stimulation parameter for pain control, since the amplitude has to be maintained within a narrow band which produces a sensation of paresthesia. If the amplitude is allowed to decrease as lead impedance or pulse width are increased, ineffective therapy may result.

Another deficiency found in prior art, multiple-channel neural stimulators, is that all electrodes within a given channel receive the same pulse amplitude, width and rate making steering of the electric field a difficult, imprecise and time consuming clinical procedure.

Another deficiency found in prior art neural stimulators, is that patients wearing spinal cord stimulators often experience periods of under stimulation or over stimulation due to postural changes, frequently requiring reprogramming of the pulse amplitude until paresthesia is reestablished.

Another deficiency found in prior art neural stimulators has to do with their conventional hardware architecture which can only control a limited number of channels and electrodes, limiting therapy effectiveness.

Still another deficiency found in prior art neural stimulators, is the lack of capability to sense and respond to biological signals. The effectiveness of neural stimulators may be improved if delivery of medical therapy is started or stopped upon sensing a specific biological signal.

SUMMARY OF THE INVENTION

It is therefore an objective of the present invention to provide an implantable tissue stimulator with a "modular" architecture, in which a single master controller services an unlimited number of I/O modules, each electrode in each I/O module being capable of being programmed to deliver stimulation pulses having different amplitude, pulse width and rate.

It is another objective of the present invention to provide an I/O module design which is capable of being non-invasively programmed to stimulate, in either, "isolation" or "combination" mode. In the "isolation" mode, stimulation currents are confined to the selected electrodes. In the "combination" mode, the stimulation currents are allowed to traverse to electrodes between two or more I/O module(s) in order to achieve a steerable electric field by forming current vectors between two or more stimulation channels.

It is another objective of the present invention to provide, in a tissue stimulator, the ability to non-invasively program each channel in each I/O module to a different amplitude employing a single and conventional DC/DC converter, by (a) providing an amplitude holding capacitor for each channel, (b) operating a single DC/DC converter to charge the first holding capacitor until the programmed voltage for the first channel is reached, and (c) repeating step "b" for the second, third and fourth holding capacitor and channel.

It is another objective of the present invention to provide a "programmable" biological sensor for use in an implantable tissue stimulator, wherein (a) a "first" digital format representing the time and frequency domain of a desired biological signal is programmed into an electronic memory within the implanted stimulator, (b) analog signals detected by an electrode placed proximal to the tissue of interest are amplified, (c) the amplified analog signal is converted into a "second" digital format conserving the original time and amplitude domains of the analog signal, (d) the "second" digital format is compared to the "first" digital format, and (e) upon a positive comparison, the implantable tissue stimulator (1) initiates or terminates a predetermined stimulation schedule, or (2) modifies an on-going stimulation schedule, or (3) initiates the delivery of a predetermined volume of a drug or medicine to a specific site, or (4) telemeters specific commands to another implanted or external device to initiate delivery of medical therapy.

Thus, according to the present invention there is provided a tissue stimulating system comprising (a) a master controller including a micro-controller, non-volatile memory, circuitry for receiving signals down-linked by external devices representing commands or program data and circuitry for up-linking signals representing stored data or commands to external devices; (b) two or more I/O modules each having two or more stimulating electrodes, circuitry for delivering electrical pulses of different amplitude, pulse width and rate to each electrode, and circuitry for powering the circuitry driving each electrode from an isolated power source; and, (c) a bidirectional bus carrying data and control signals between the master controller and the I/O modules.

A useful application for such a stimulation system is one that is responsive to the detection of a biological signal, is one in which a specific nerve is stimulated followed by searching for the corresponding brain's evoked potential. Thereby, a stimulation system with biofeedback can be arranged, such that, periodically the pulse amplitude is first zeroed and then slowly increased until a specific evoked potential is detected, resulting in automatically establishing the new threshold of paresthesia without patient or physician intervention.

In another useful application for a biofeedback stimulator, a glucose sensor is connected to the input of one of the I/O modules, whereby the output signal of the sensor represents the glucose level. The signal is measured by an A/D converter and if the measured glucose level is below a predetermined value, the master controller telemeters start and stop command to an implantable infusion pump to deliver a volume of insulin to the patient based on the measured level of glucose.

It is another objective of the present invention to provide a closed-loop output circuit design in which the delivered pulse amplitude is measured and compared, on a real-time basis, with the desired or programmed amplitude and the delivered amplitude is adjusted as required until it equals the programmed amplitude, in order to compensate for changes in pulse width, electrode impedance, and aging of components.

It is another objective of the present invention to provide circuitry for measuring and recording in memory lead impedance values upon detecting a predetermined command, whereby said command may occur when the patient adjusts one or more of the stimulation parameters, or alternatively may occur at specific time intervals, in order to later telemeter, to an external unit, a histogram for each stimulation parameter for evaluation by the physician.

It is another objective of the present invention to provide circuitry for recording in a memory within the implanted tissue stimulator, the value for each adjustment of any stimulation parameters along with the time and date when the adjustments were made, in order to later telemeter to an external unit a histogram for each stimulation parameter for evaluation by the physician.

It is another objective of the present invention to provide an independent power source in each module which (1) is recharged by the main power source in between stimulus pulses and (2) is disconnected from the main power source during delivery of the stimulus pulses in order to provide isolation between channels.

It is another objective of the present invention to provide circuitry for delivering stimulus pulses to each electrode having different pulse width and rate.

It is still another objective of the present invention to provide circuitry for non-invasively selecting the regulation of the stimulus pulses to be constant current or constant voltage.

BRIEF DESCRIPTION OF THE DRAWINGS

FIG. 10D is an equivalent circuit for still another form of simultaneous stimulation in an "ISOLATION" mode.

DESCRIPTION OF THE PREFERRED EMBODIMENT(S)

Figure 1:
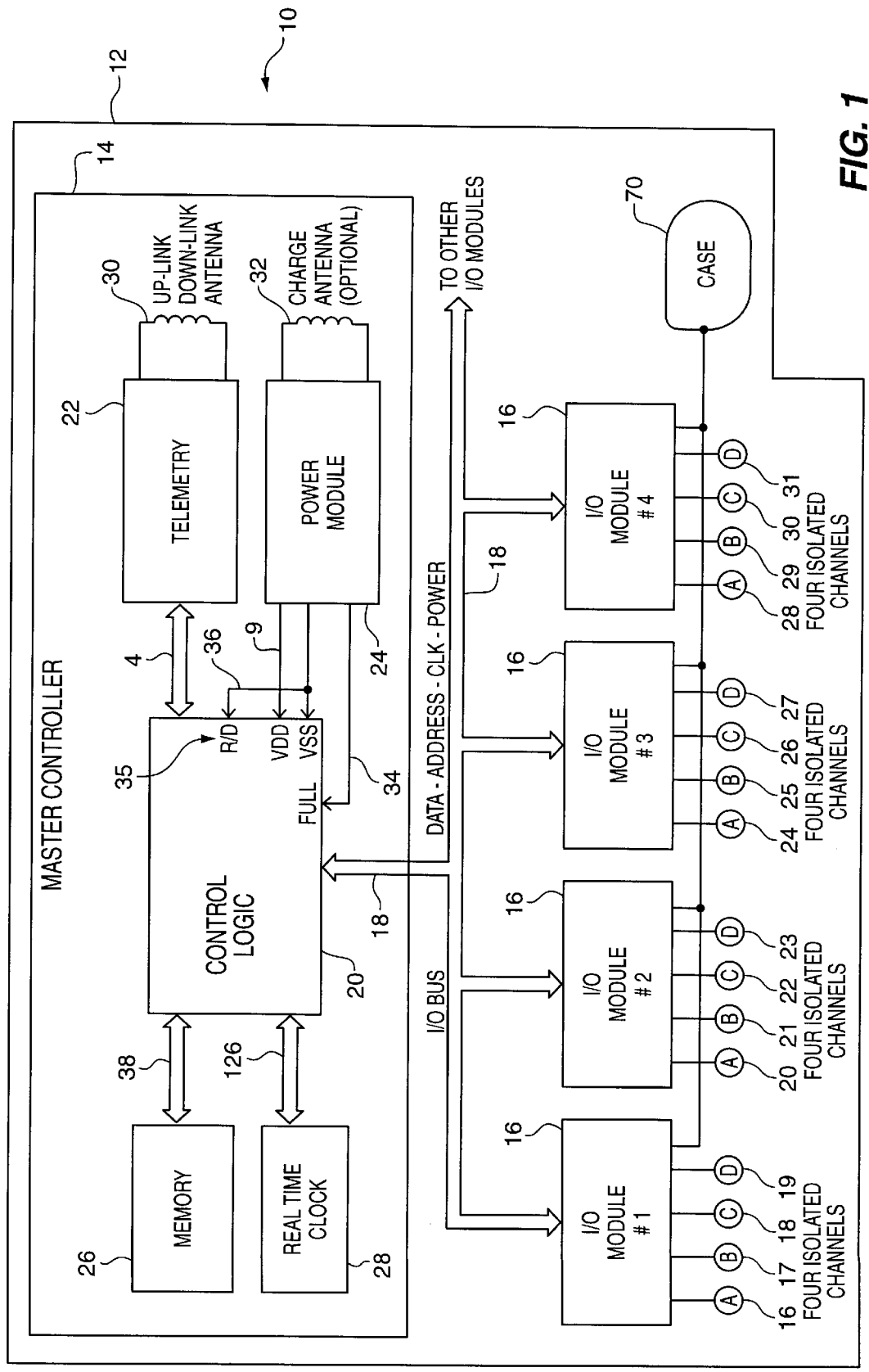
FIG. 1 is a block electrical schematic circuit diagram of the electrical circuit for the implantable, tissue stimulator of the present invention.

Referring now to FIG. 1 in greater detail, there is illustrated a block diagram 10 for a subcutaneously implanted modular tissue stimulator 12. The modular tissue stimulator 12 encompasses one master controller 14, any practical number of I/O modules 16, and a bi-directional I/O bus 18 carrying data, address, power and clock between the master controller 14 and each I/O module 16.

Referring again to FIG. 1, the primary elements of the master controller 14 are micro-controller 20, telemetry circuit 22, power module 24, non-volatile memory 26, real time clock 28, and I/O bus 18 connected as shown. The master controller 14 is used to (a) communicate with an external programmer device (not shown) which the physician uses to program the stimulation values for each channel A, B, C or D, (b) to transmit to the appropriate I/O module 16 the stimulation values, (c) to store in the non-volatile memory 26 the stimulation values, (d) to keep time of day and calendar date, (e) to received data from any I/O module 16 to be up-linked, and (f) to up-link specific commands to an external pager (not shown), the commands to be displayed by the pager device. Examples for these commands are: "take medication", "low battery in stimulator", "start insulin infusion", etc. Stimulation values are addressed and delivered to each I/O module 16 via bus 18.

Micro-controller 20 may be any commercially available μcontroller capable of operating on low power and voltage and incorporating at least one A/D converter port.

Telemetry circuit 22 is a conventional telemetry circuit known to the art using pulse interval modulation technique to encode data, and incorporating an inductor 30 to up-link data and receive down-linked signals.

Power module 24 can be (a) as simple as a primary, implantable grade battery, or (b) an optional rechargeable power source with a charging circuit used to convert RF power received by an inductor 32 into a DC voltage, such as the system disclosed in U.S. patent application Ser. No. 08/690,968 or (c) a pure RF powered system such as the system disclosed in U.S. patent application Ser. No. 08/763,000. In the case of the optional rechargeable battery, an output 34 is used to signal micro-controller 20 when the battery reaches a fully charged state. Also, the VSS voltage level is connected to an A/D port 35 of the micro-controller 20 via line 36 in order to measure the battery voltage to determine the condition of the battery in power module 24.

Non-volatile memory 26 is a low power, low voltage, serial EEPROM which is connected to the micro-controller 20 via a bus 38. Bus 18 carries address, data, power (VDD and ground), and clock to all I/O modules 16.

Figure 2:
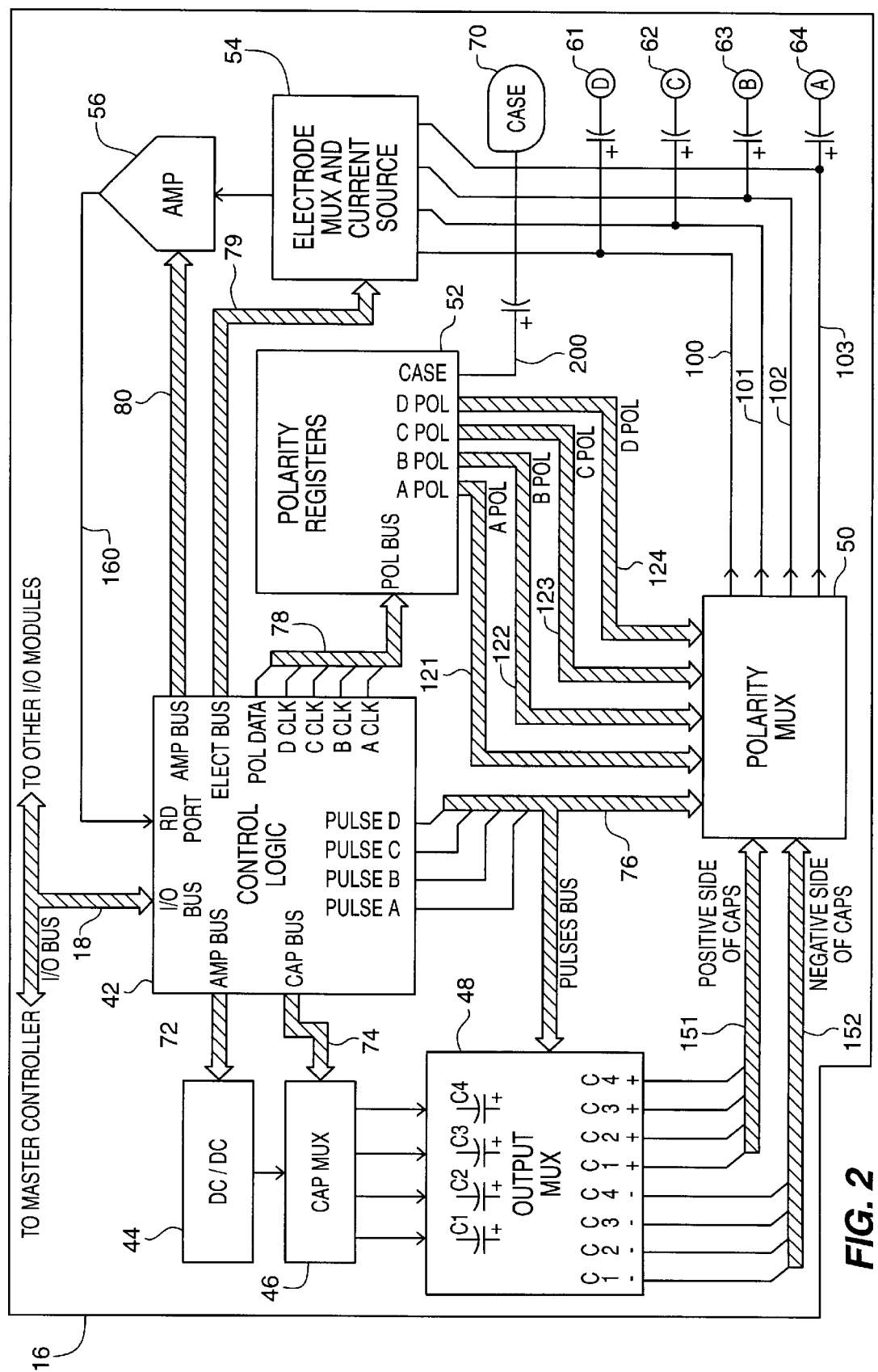
FIG. 2 is a block electrical schematic circuit diagram of the electrical circuit for an I/O module of the implantable, tissue stimulator shown in FIG. 1.

Referring now to FIG. 2, there is illustrated therein a block diagram 40 for one I/O module 16 is illustrated therein. The function of the I/O module 16 is to operate four (4) channels A, B, C and D of stimulation (one electrode per channel), each channel having independently programmable pulse parameters. Therefore, each channel A, B, C and D can be programmed to (a) different amplitude, rate and pulse width, (b) same rate but different amplitude and pulse width, (c) same rate and pulse width but different amplitude, (d) same rate and amplitude but different pulse width, (e) same amplitude and pulse width but different rate, or (f) same rate, pulse width and amplitude, (g) same pulse width but different amplitude and rate, or (h) same amplitude but different pulse width and rate.

Referring to FIG. 2, the major components of each I/O module 16 include a control logic 42, a DC/DC converter 44, a capacitor multiplexer 46, an output multiplexer 48, including four holding capacitors C1, C2 C3 and C4, a polarity multiplexer 50, polarity registers 52, electrode multiplexer and current source 54, an amplifier 56, stimulating electrodes (channels) 61, 62, 63 and 64, and a case electrode 70.

Control logic 42 is used to (1) control via an amplitude bus 72, the DC voltage at the output of the DC/DC converter 44, (2) connect via a capacitor bus 74, any combination of holding capacitors C1, C2, C3 and/or C4 to the output of the DC/DC converter 44, (3) connect via pulses bus 76, holding capacitors C1, C2, C3 and C4 to either (i) capacitor multiplexer 46 during charging to the programmed pulse amplitude or (ii) to the polarity multiplexer 50 during delivery of the stimulus pulse, (4) load via a bus 78, polarity registers 52 with the polarity selection for electrodes 61, 62, 63 and 64 plus case electrode 70, (5) switch via polarity multiplexer 50, the positive and negative sides of holding capacitors C1, C2, C3 and C4 to the appropriate electrodes 61, 62, 63 and 64 plus case 70 in order to achieve the programmed polarity, (6) control via an electrode bus 79, electrode multiplexer and current source 54 to select the appropriate electrode for detecting biological signals or to measure electrode impedance, (7) and control via an amplifier bus 80, the gain and pass band of the amplifier 56.

Figure 3:
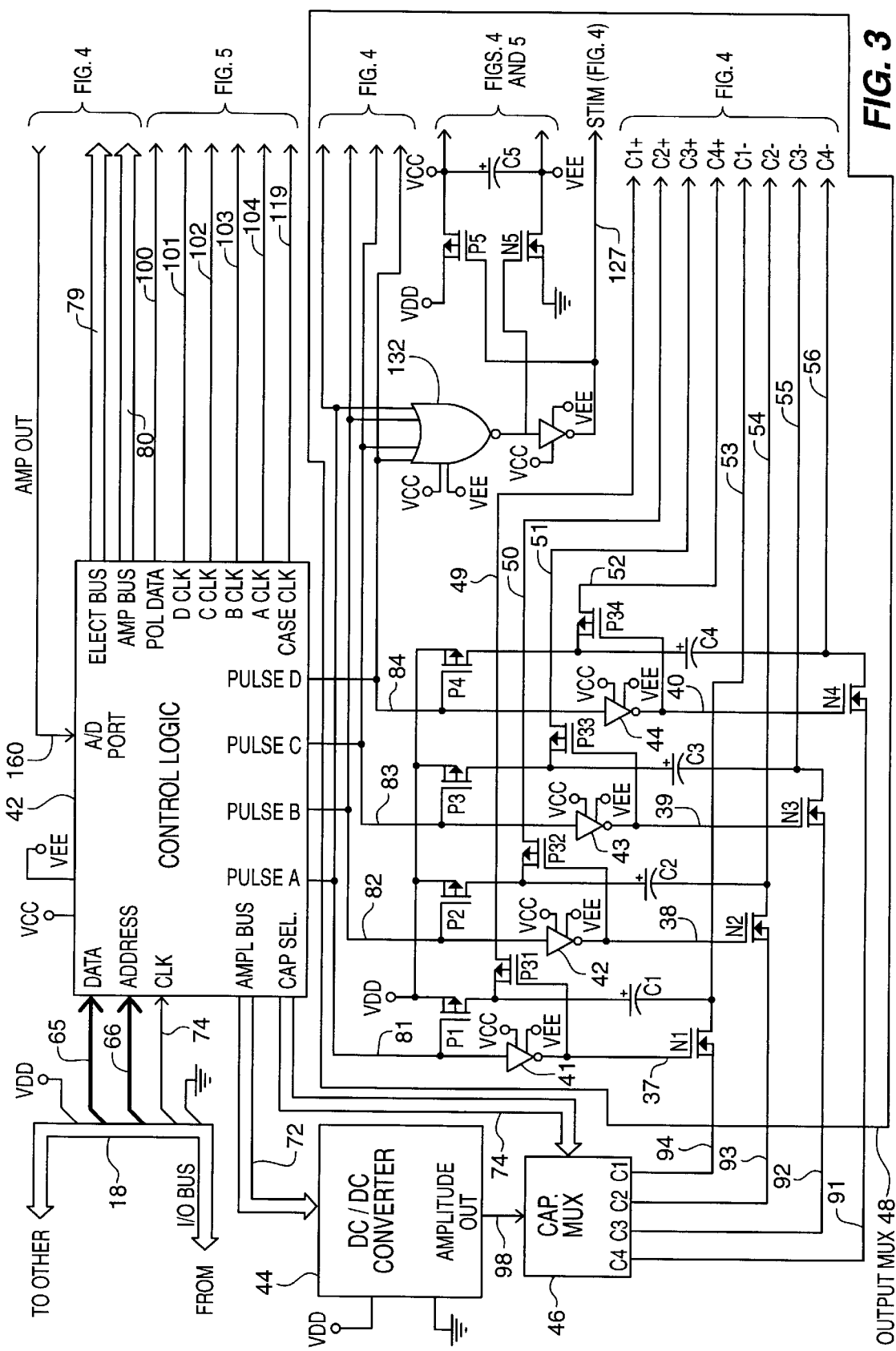
FIG. 3 is a block electrical schematic circuit diagram of the electrical circuit for an output multiplexer of the I/O module shown in FIG. 2.

Referring now to FIG. 3, there is illustrated therein an electrical schematic circuit diagram for the output multiplexer 48. The circuit utilizes one amplitude holding capacitor C1, C2, C3 or C4 per channel A, B, C and D. Each capacitor can be independently charged to a different voltage amplitude using a single DC/DC converter 44. The major components of this circuit are control logic 42, the DC/DC converter 44, the capacitor multiplexer 46, and a network of transistors N1–N4, P1–P4 and P31–P34, used to isolate each holding capacitor from the other holding capacitors during delivery of each stimulus pulse. Ports 81–84 from control logic 42 are used to generate four independent pulses, one per channel.

These four pulses can be set to occur simultaneously (same rate), in synchrony but after a predetermined delay between them (same rate) or asynchronous to each other (different rate).

Programming data for these four pulses (rate, pulse width and delay between pulses) is routed by the master controller 14 via bus 18 to the addressed I/O module 16. Also, bus 18 carries the operating power and the clock for each I/O module 16.

DC/DC converter 44 can be a conventional "ratioed capacitor charge pump" known to the art, whereby during the first half of a pump cycle, a small capacitor is charged to a regulated voltage and during the second half, the charge in the small capacitor is dumped into a much larger capacitor called the amplitude holding capacitor. The capacitance ratio between the "small" and "holding" capacitors determines the voltage step per pump cycle.

For example, if a "small" capacitor having 0.1 $\mu$F and a "holding" capacitor having 10 $\mu$F were used, whereby the "small" capacitor is charged up to 5.0 volts, the voltage at the "holding" capacitor will rise 50 mV each time the "small" capacitor is dumped into the "holding" capacitor.

In one unique aspect of this invention, capacitor multiplexer 46 is used to sequentially direct the output of the DC/DC converter 44 to each of the four "holding" capacitors via lines 91–94 (one capacitor per channel).

The amplitude bus 72 is used to select the output voltage of the DC/DC converter 44 representing the voltage amplitude for each of the four "holding capacitors" C1–C4 after they are fully charged. During charging of a "holding" capacitor to the programmed voltage amplitude for the corresponding channel, transistors P1, P2, P3 or P4 are used to switch the + side of the capacitor to the + side of the power source while the − side of the capacitor is connected to the output of the DC/DC converter 44 via the capacitor multiplexer 46 and the transistors N1, N2, N3 or N4.

Figure 4:
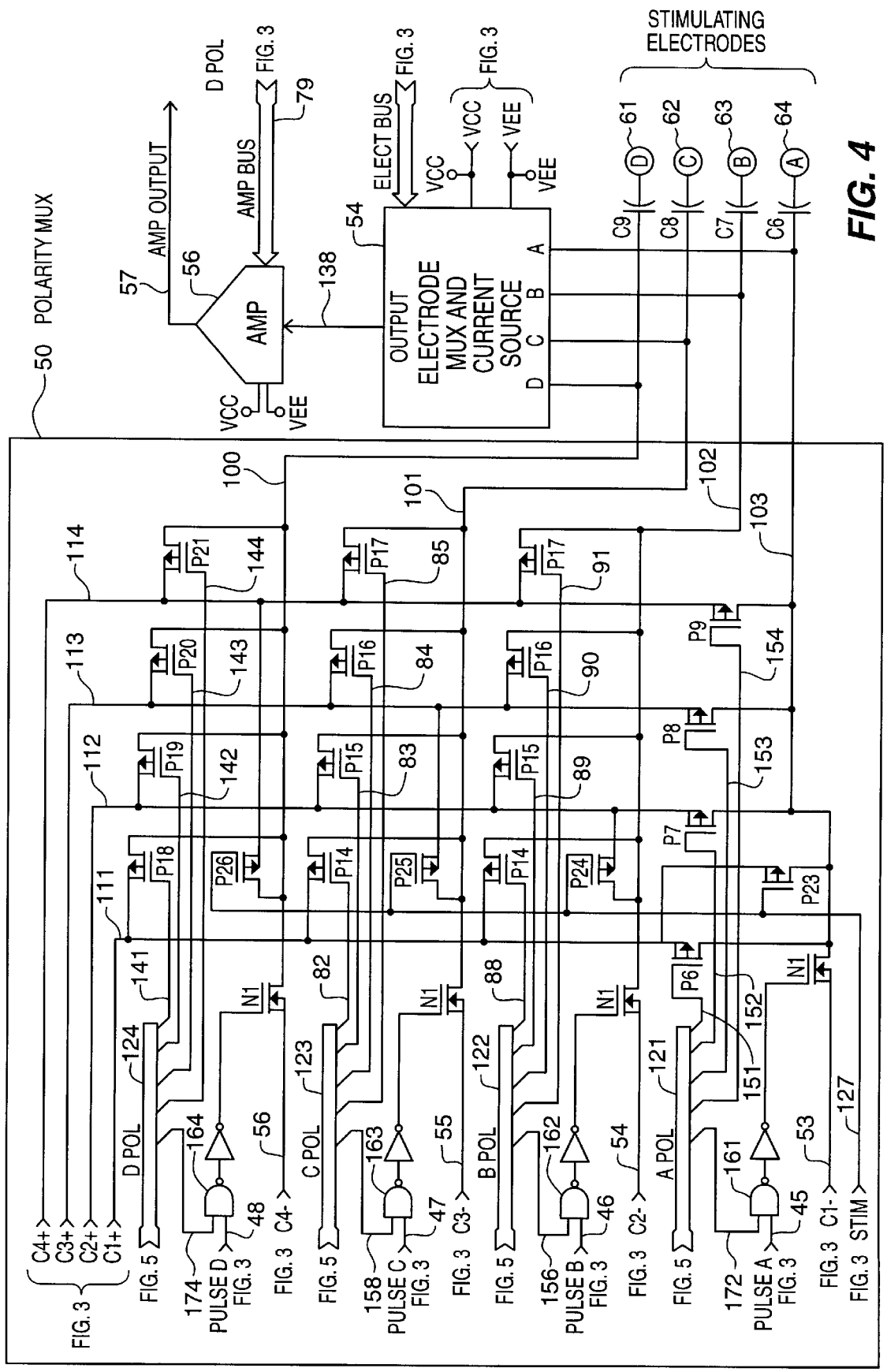
FIG. 4 is a block electrical schematic circuit diagram of the electrical circuit for a polarity multiplexer of the I/O module shown in FIG. 2.
Figure 5:
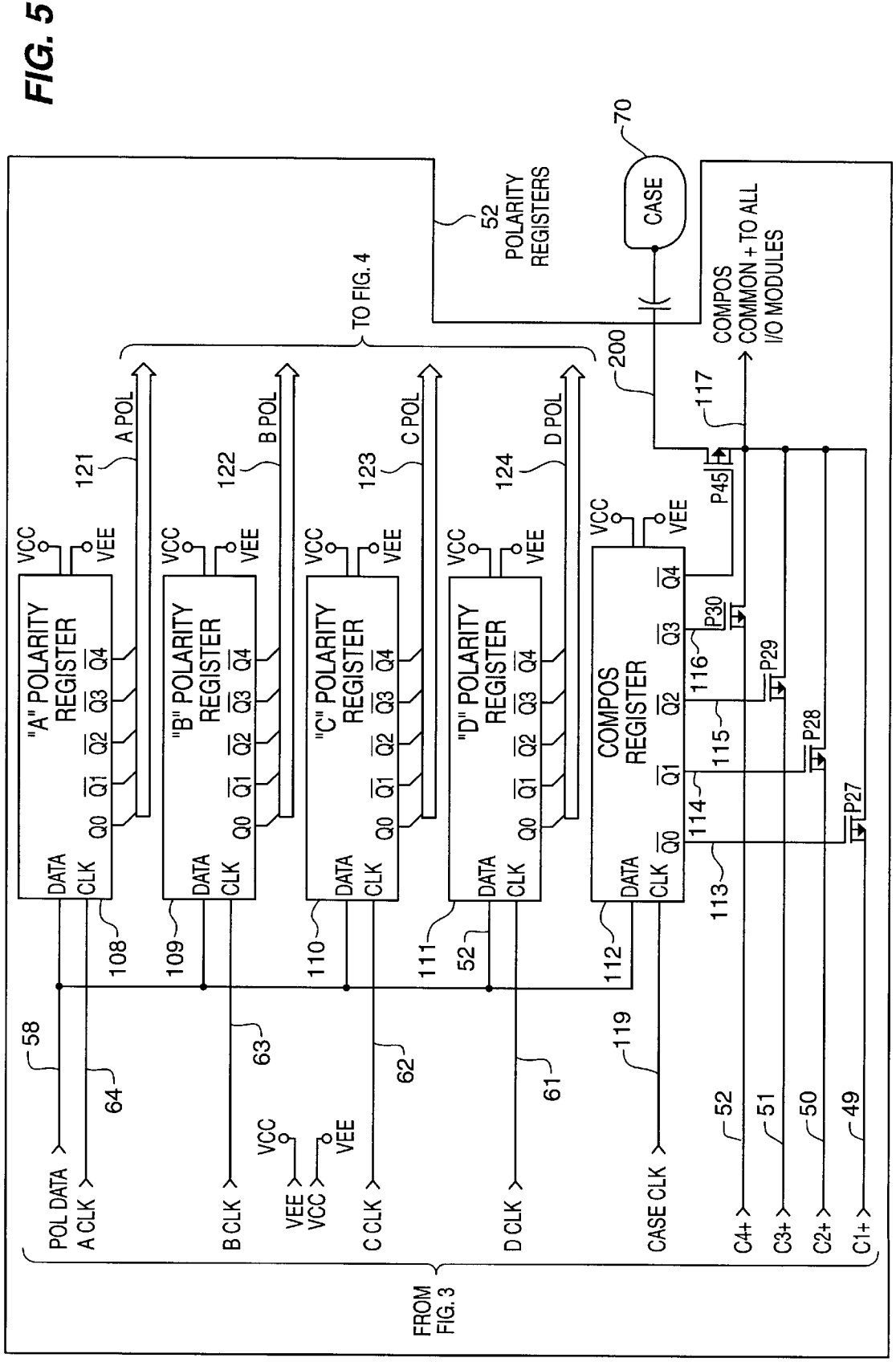
FIG. 5 is a block electrical schematic circuit diagram of the electrical circuit for the polarity registers of the I/O module shown in FIG. 2.

Referring to FIG. 3, line 100 is a data line which is used to load a 1 or 0 into the polarity registers of FIG. 5 which control the polarity (positive, negative or off) of each of the four stimulating electrodes in FIG. 4. Lines 101–104 are used to clock the value of line 100 into the polarity registers 52 of FIG. 5.

Referring now to FIG. 4, a block diagram for a polarity multiplexer 50 is illustrated therein. This circuit is utilized to select the polarity for each of the four electrodes 61, 62, 63 and 64 plus case electrode 70. Near the top of the drawing, lines 111–114 are connected to the positive side of holding capacitors C1, C2, C3 and C4, respectively. For each electrode there are four PMOS transistors which, when that electrode is programmed positive, are used to select which holding capacitor(s) will "source" current. Likewise, for each electrode there is one NMOS transistor N6, N7, N8 or N9 which, when that electrode is programmed negative, are used to connect the negative side of the corresponding holding capacitor to the electrode to provide a "sink" current.

Referring to FIG. 5, an electrical schematic circuit diagram for the polarity registers 52 is illustrated therein. A total of five registers are used, one for each electrode 61–64 and 70. These registers 52 are loaded by the control logic 42 with the polarity assigned to each electrode, and generate the control lines regulating polarity multiplexer 50. Note that for A, B, C and D polarity registers, buses 121–124 exit the registers, respectively. These buses return to FIG. 4 to control a transistor matrix employed to switch capacitors C1, C2, C3 and C4 to the selected electrode(s).

The drain of transistor P45 is connected to the case 70. The purpose of CMOS is to provide a common positive (+) line to where the positive side of any holding capacitor (C1–C4) in any I/O module 16 can be connected so that a current path between two modules can be established.

Figure 6:
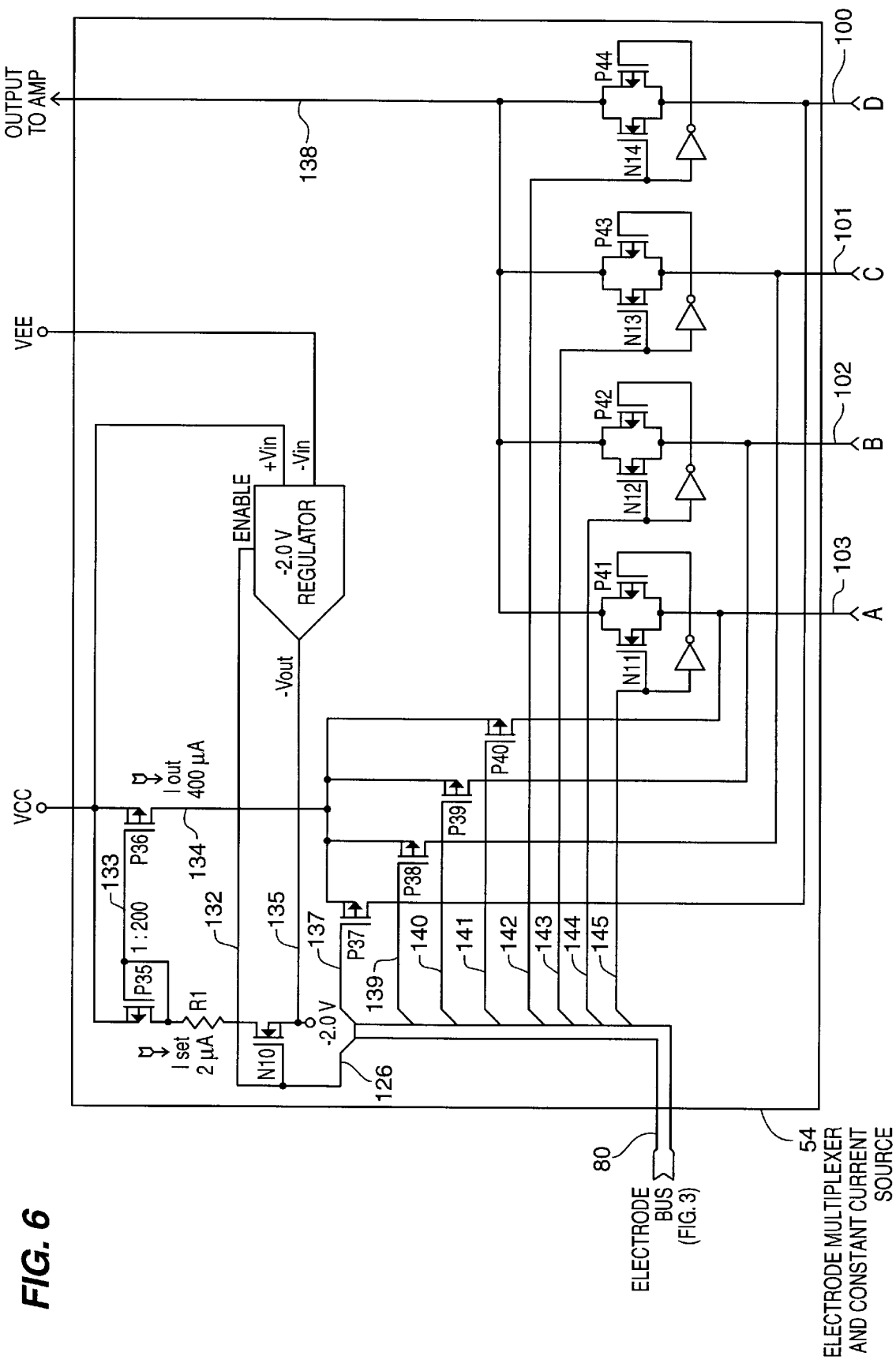
FIG. 6 is a block electrical schematic circuit diagram of the electrical circuit for the electrode multiplexer and constant current source of the I/O module shown in FIG. 2.

Referring to FIG. 6, an electrical schematic circuit diagram is illustrated therein for the electrode multiplexer and current source 54. This design provides for a constant current source of 400 $\mu$A which can be applied to any selected electrode in order to facilitate an accurate measurement of lead impedance. Line 126 within electrode bus 80 is switched to a 1 by control logic 42 to enable measuring lead impedance. This turns on transistor N10 which allows transistors P35 and P36 to form a current mirror whereby 2 $\mu$A flows through P35 causing P36 to source 400 $\mu$A. Control logic 42 also will switch on either P37, P38, P39 or P40 in order to connect current source P36 to the electrode whose impedance is about to be measured. During the next stimulus pulse, the voltage drop occurring across P36 will be buffered by amplifier 56 and measured by the A/D port of control logic 42. Electrode impedance can then be calculated by dividing the voltage drop across P36 by 400 $\mu$A.

One unique aspect of the present invention, is the capability of the stimulator 12 to generate from the main power source in the master controller 14, an isolated power source to power each I/O module 16, in order to support the logic functions of each I/O module while at the same time providing electrical isolation between each I/O module 16. Referring to FIG. 3, NOR gate 132 is inactive when Pulse A, Pulse B, Pulse C and Pulse D are all at logic 0, keeping transistors NS and P5 conducting and connecting capacitor C5 to the main power source in the master controller. Notice that all logic circuitry in the I/O module 16 is powered by VCC and VEE. NOR gate 132 becomes active when either, Pulse A, Pulse B, Pulse C or Pulse D switch to a logic 1. For the duration of these pulses, transistors N5 and P5 are switched off effectively isolating the I/O module 16 from the main power supply in master controller 14, allowing C5 to exclusively power the I/O module 16.

Figure 8:
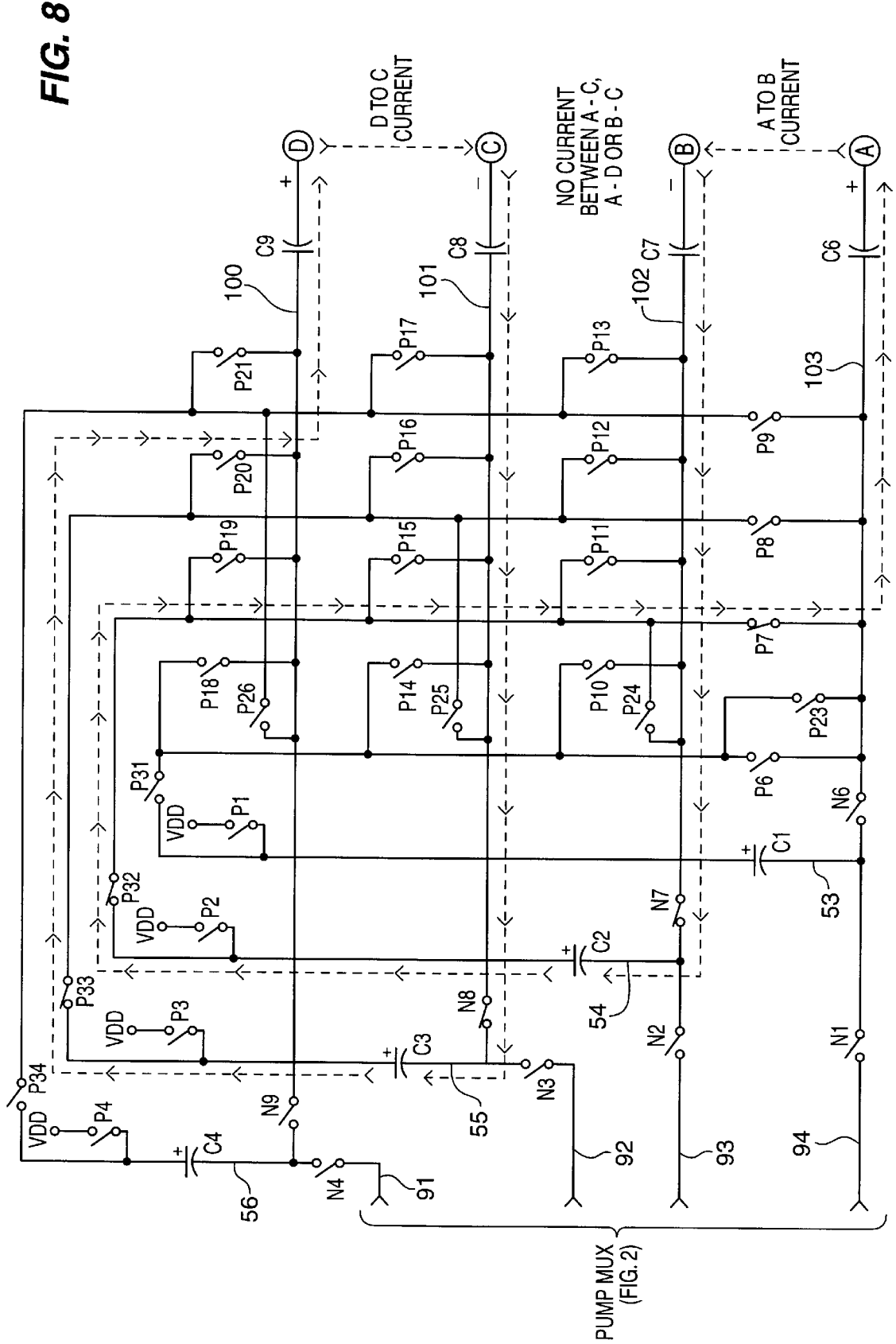
FIG. 8 is an equivalent circuit for one form of simultaneous stimulation in an "ISOLATION" mode.

Another unique aspect of the present invention, is the capability of the stimulator 12 to program electrodes to the "isolation" or the "combination" mode. When two pairs of electrodes are programmed in the "isolation" mode, the current path between one pair is isolated from the current path in the other pair. No current traverses from one pair of electrodes to the other pair, even when each pair is programmed to a different amplitude and both stimulus pulses occur simultaneously. One example of stimulating in the "isolation" mode is illustrated in FIG. 8, where the tissue stimulator 12 is programmed to the "isolation" mode, electrodes D and A are programmed positive and B and C are programmed negative. In this example two autonomous current paths will result, one from A (+) to B (−) and the other from D (+) to C (−). This is possible because there is one amplitude holding capacitor per electrode (channel), and in the isolation mode the positive side of each capacitor can be switched to only one electrode.

The manner in which the result is obtained is explained below. Referring to FIG. 4, for this example line 143 will be programmed to 0, turning on P20 which connects the + side of C3 to electrode D (positive polarity). Lines 141, 142 and 144 will be programmed to 1, keeping P21, P19 and P18 off. Likewise, line 152 will be programmed low, turning on P7 which connects the + side of C2 to electrode A (positive polarity). Lines 151, 153 and 154 will be programmed to 1, keeping P6, P8 and P9 off. Now since electrode B was programmed negative, line 156 is set to 1 and, during "Pulse B" time, N7 is switched on and P24 is switched off, thus connecting electrode B to the negative side of C2 (negative polarity). Likewise, since electrode C was also programmed negative, line 158 is set to 1 and, during "Pulse C" time, N8 and P25 are switched on and off, respectively, thus connecting electrode C to the negative side of C3 (negative polarity).

Referring to the equivalent circuit of FIG. 8, in summary for this example were A was paired with B, during the stimulus pulse at electrode B the negative side of capacitor C2 is momentarily switched over to electrode B while C2's positive side is connected to electrode A, resulting in current leaving the positive plate of C2 into electrode A (+), flowing through the tissue into electrode B (−) and into the negative plate of C2. Similarly, a separate current flows from the positive side of C3 into electrode D (+), through the tissue into electrode C (−) and into the negative side of C3. As illustrated in FIG. 8, the two current paths are isolated from each other because capacitors C2 and C3 are acting as small, independent power supplies for each electrode pair during each stimulus pulse. Even if the two stimulus pulses were to occur simultaneously, current can't traverse from A/B into C/D or vice versa, because capacitors C2 and C3 are isolated from each other during each stimulus pulse. Obviously, during each stimulus pulse the output coupling capacitors C6, C7, C8 and C9 will accumulate a charge which needs to be dumped before the next stimulus pulse. In order to prevent electrode corrosion, a balanced zero net DC current must be achieved by including the same electrode/tissue interface in the current path during dumping of the accumulated charges.

Referring to FIG. 3, upon "pulse B" switching low transistor P32 will switch off disconnecting the + side of C2 from electrode A. Referring to FIGS. 4 and 8, when P24 turns on while P7 is also on, the result is that electrodes A and B are short circuited in between pulses, allowing C6 and C7 to dump their charges through the tissue. Similarly, referring to FIG. 3, upon "pulse C" switching low transistor P33 will switch off disconnecting the + side of C3 from electrode C. Referring to FIGS. 4 and 8, note that when P25 turns on while P20 is also on, the result is that electrodes C and D are short circuited in between pulses, allowing C8 and C9 to dump their charges through the tissue.

Figure 9:
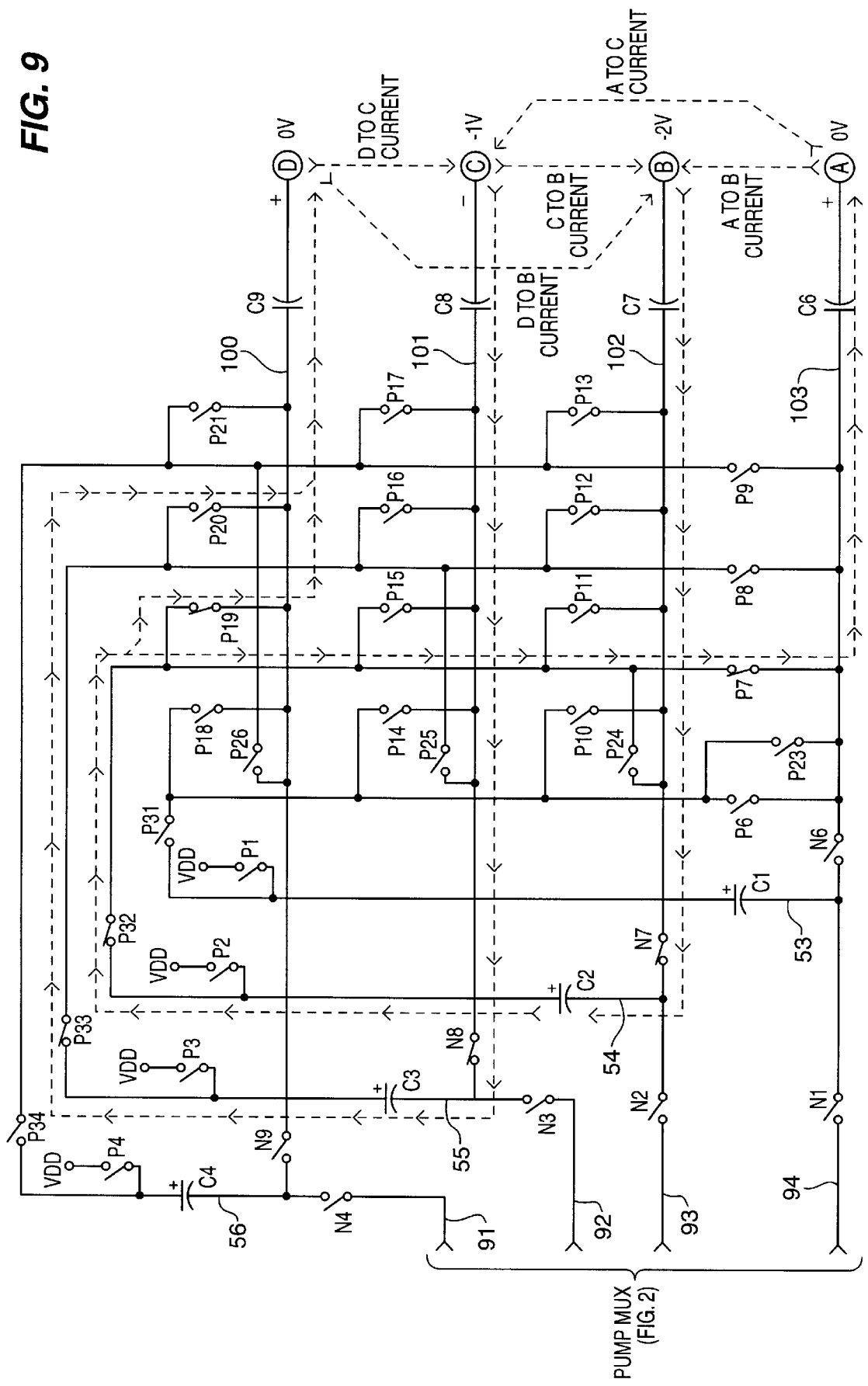
FIG. 9 is an equivalent circuit for one form of simultaneous stimulation in a "COMBINATION" mode.

Now, looking at the example illustrated in FIG. 9 where electrodes A and D are programmed positive, B and C are programmed negative but currents are allowed to traverse between all electrodes ("combination" mode), in order to steer the electric field closer to some specific tissue and to control the size electric field. The connections for this example are similar to those of FIG. 8, except that transistors P19 and P7 are programmed "on" in order to connect together the positive sides and capacitors C2 and C3 allowing currents between C2 and C3 to traverse. Note that in FIG. 9 electrode B was programmed more negative than electrode C resulting in an electric field which is broader than that in FIG. 8, but with a higher current density at electrode B than at electrode C.

FIGS. 10A, 10B, 10C and 10D illustrate the current flow in the "isolation" mode when the "case" (hermetic housing) is programmed as the positive electrode and channels A, B, C and D are programmed negative. In this example, channel A is programmed to −4 volts, channel B to −3 volts, channel C to −2 volts and channel D to −1 volt. A timing diagram is incorporated in each figure to illustrate when the electrodes are positive, negative or open circuit (off) during delivery of the programmed stimulation schedule.

Figure 10A:
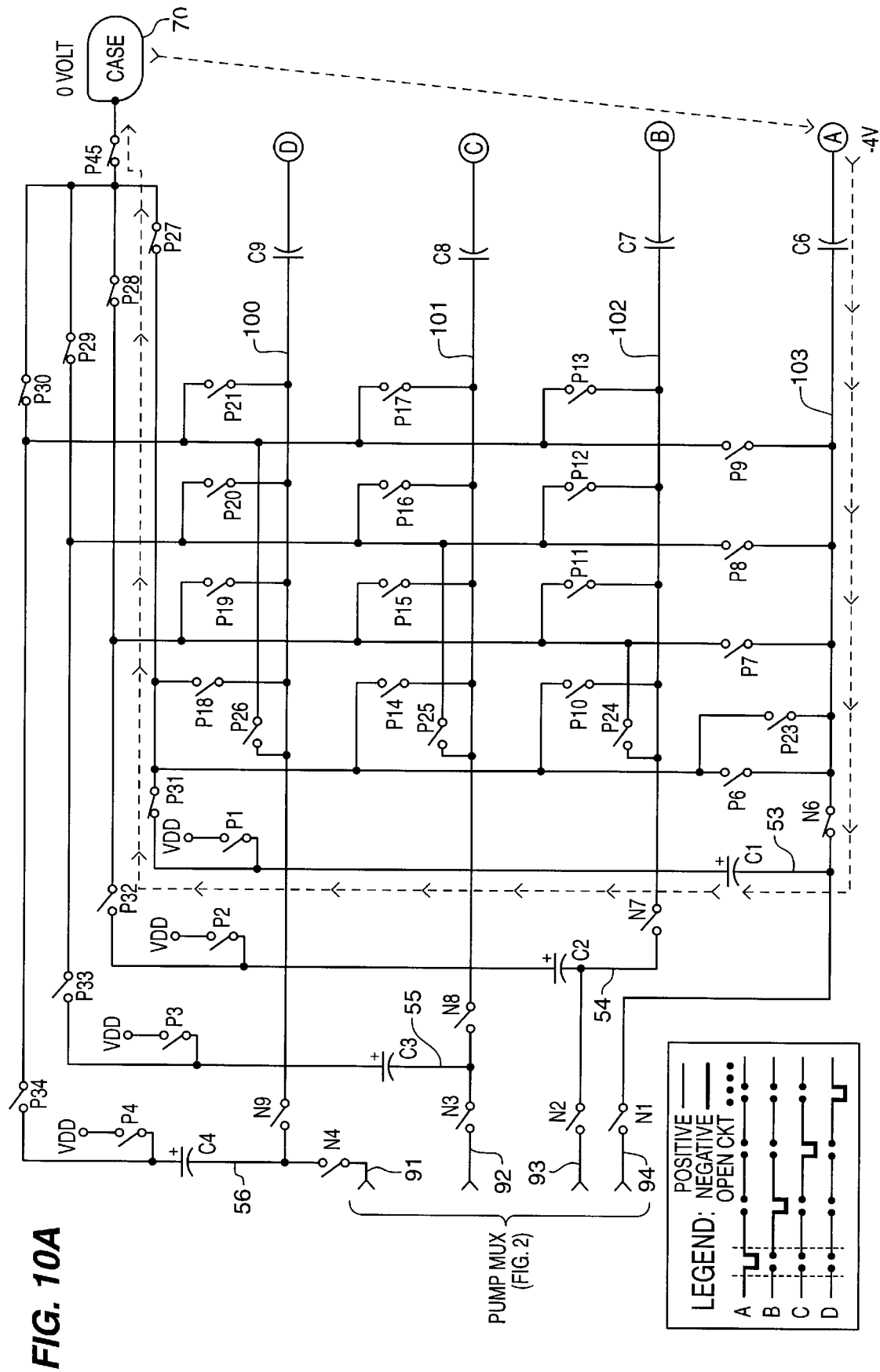
FIG. 10A is an equivalent circuit for another form of simultaneous stimulation in an "ISOLATION" mode.

FIG. 10A illustrates that during delivery of channel A stimulus pulse, only a single current path from the case (zero volts) to electrode A (−4V) is formed, with no current traversing to any other electrodes. This is possible because P27 is connecting the + side of C1 to the case and transistor N6 is connecting the − side of C1 to electrode A, thereby capacitor C1 ends up completely isolated from the other electrodes.

Figure 10B:
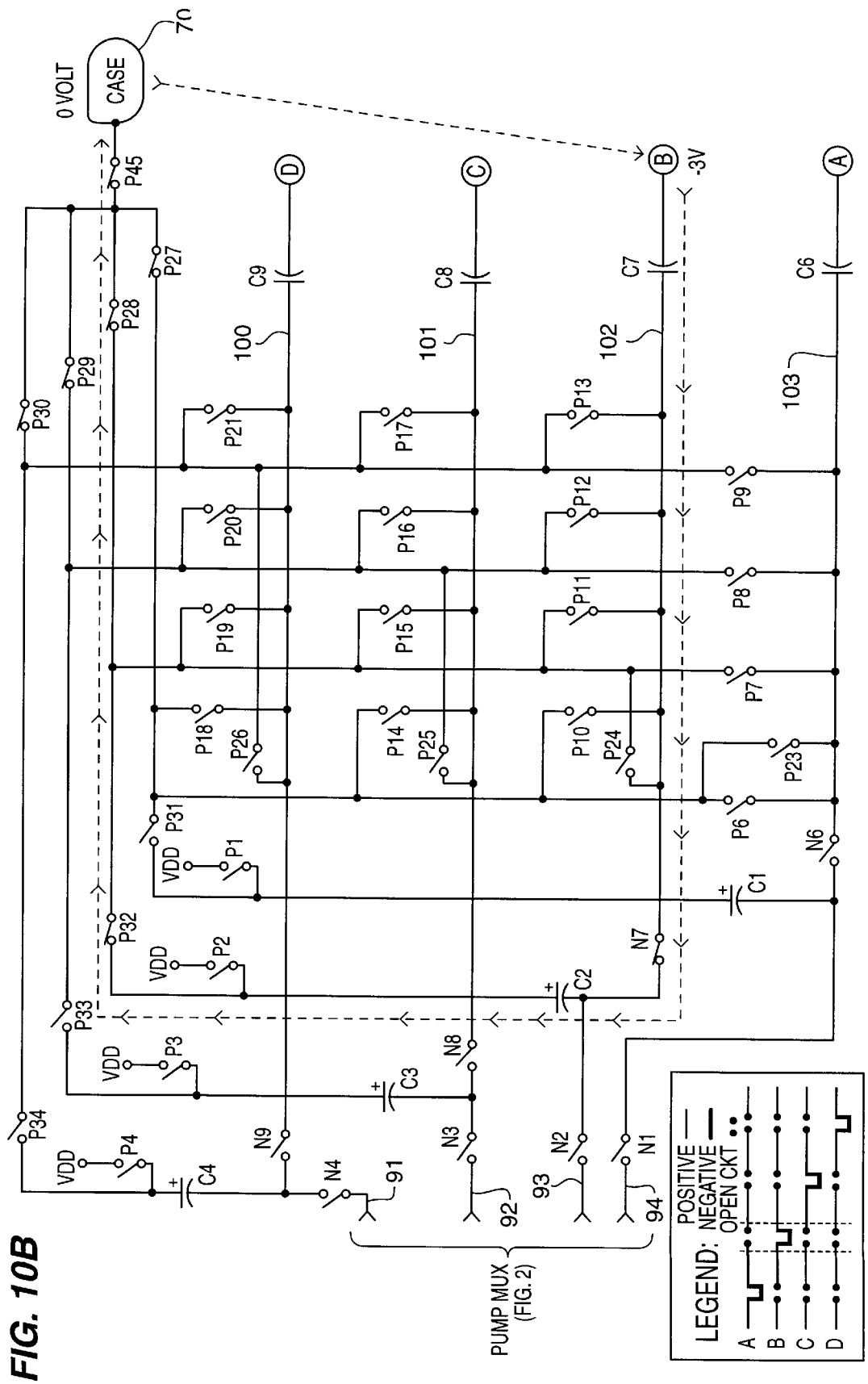
FIG. 10B is an equivalent circuit for still another form of simultaneous stimulation in an "ISOLATION" mode.

FIG. 10B illustrates that during delivery of channel B stimulus pulse, only a single current path from the case (zero volts) to electrode B (−3V) is formed, with no current traversing to any other electrodes. This is possible because transistor P28 is connecting the + side of C2 to the case and transistor N7 is connecting the − side of C2 to electrode B, thereby capacitor C2 ends up completely isolated from the other electrodes.

Figure 10C:
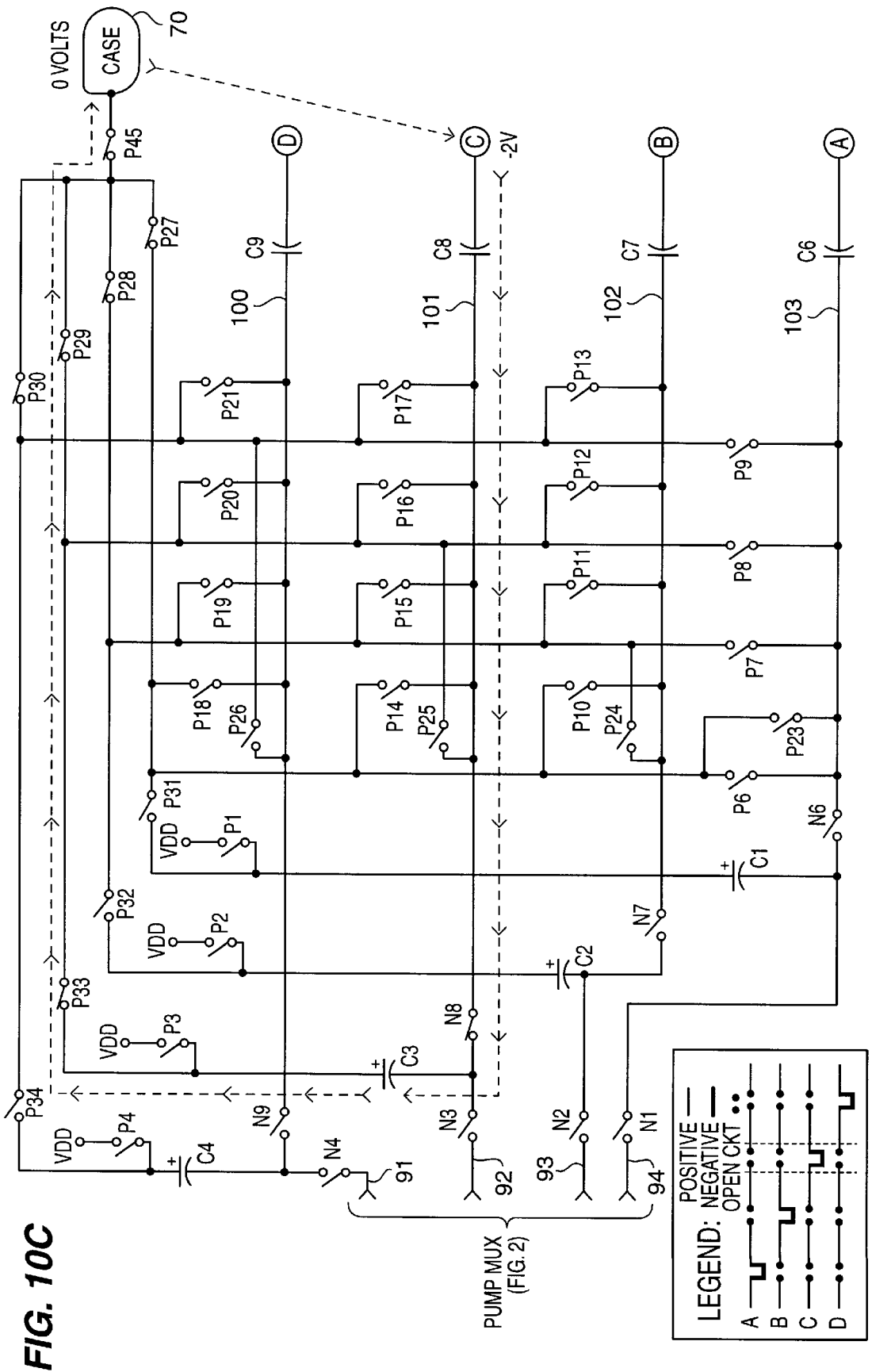
FIG. 10C is an equivalent circuit for still another form of simultaneous stimulation in an "ISOLATION" mode.

FIG. 10C illustrates that during delivery of channel C stimulus pulse, only a single current path from the case (zero volts) to electrode C (−2V) is formed, with no current traversing to any other electrodes. This is possible because transistor P29 is connecting the + side of C3 to the case and transistor N8 is connecting the − side of C3 to electrode C, thereby capacitor C3 ends up completely isolated from the other electrodes.

FIG. 10D illustrates that during delivery of channel D stimulus pulse, only a single current path from the case (zero volts) to electrode C (−1V) is formed, with no current traversing to any other electrodes. This is possible because transistor P30 is connecting the + side of C4 to the case and transistor N9 is connecting the − side of C4 to electrode D, thereby capacitor C4 ends up completely isolated from the other electrodes.

As previously explained, it is important to achieve a balanced zero net DC current through the electrodes. In the examples of FIGS. 10A, 10B, 10C, and 10D this is accomplished via transistors P23, P24, P25 and P26 which short circuit the case to electrodes A, B, C and D in between pulses. However, notice that during each stimulus pulse P23, P24, P25 and P26 are switched off to prevent any parasitic currents to the inactive electrodes.

Another unique aspect of the present invention, is the capability of the stimulator 12 to program each electrode to a different amplitude by using a single DC/DC converter 44 to sequentially charge each amplitude holding capacitors C1–C4 to a different voltage level. Referring to FIG. 3, when either stimulus drive line 81–84 is low, holding capacitors C1, C2, C3 and C4 have their + sides connected to Vdd (via transistors P1, P2, P3 and P4) and their − sides to cap multiplexer 46 (via transistors N1, N2, N3 and N4). Capacitor select bus 74 selects which holding capacitor will be connected to DC/DC converter 44, and amplitude bus 72 is used to regulate the voltage output of the DC/DC converter 44 which provides the voltage used to charge each of the four amplitude holding capacitors. Capacitor multiplexer 46 is used to pass the DC/DC converter output to the holding capacitor addressed by capacitor select bus 74. Once a holding capacitor reaches the programmed amplitude, DC/DC converter 44 stops and it's output automatically switches to a high impedance.

Referring to FIGS. 3 and 4, the pulse amplitude delivered to the electrode is measured on a real time basis via an A/D port of control logic 42 through electrode multiplexer 54 and amplifier 56.

Another unique aspect of the present invention, is the capability of the tissue stimulator 12 to provide a closed-loop output circuit capable of maintaining the programmed voltage amplitude by automatically compensating for changes in temperature, load, aging of components, pulse width and frequency.

Figure 7:
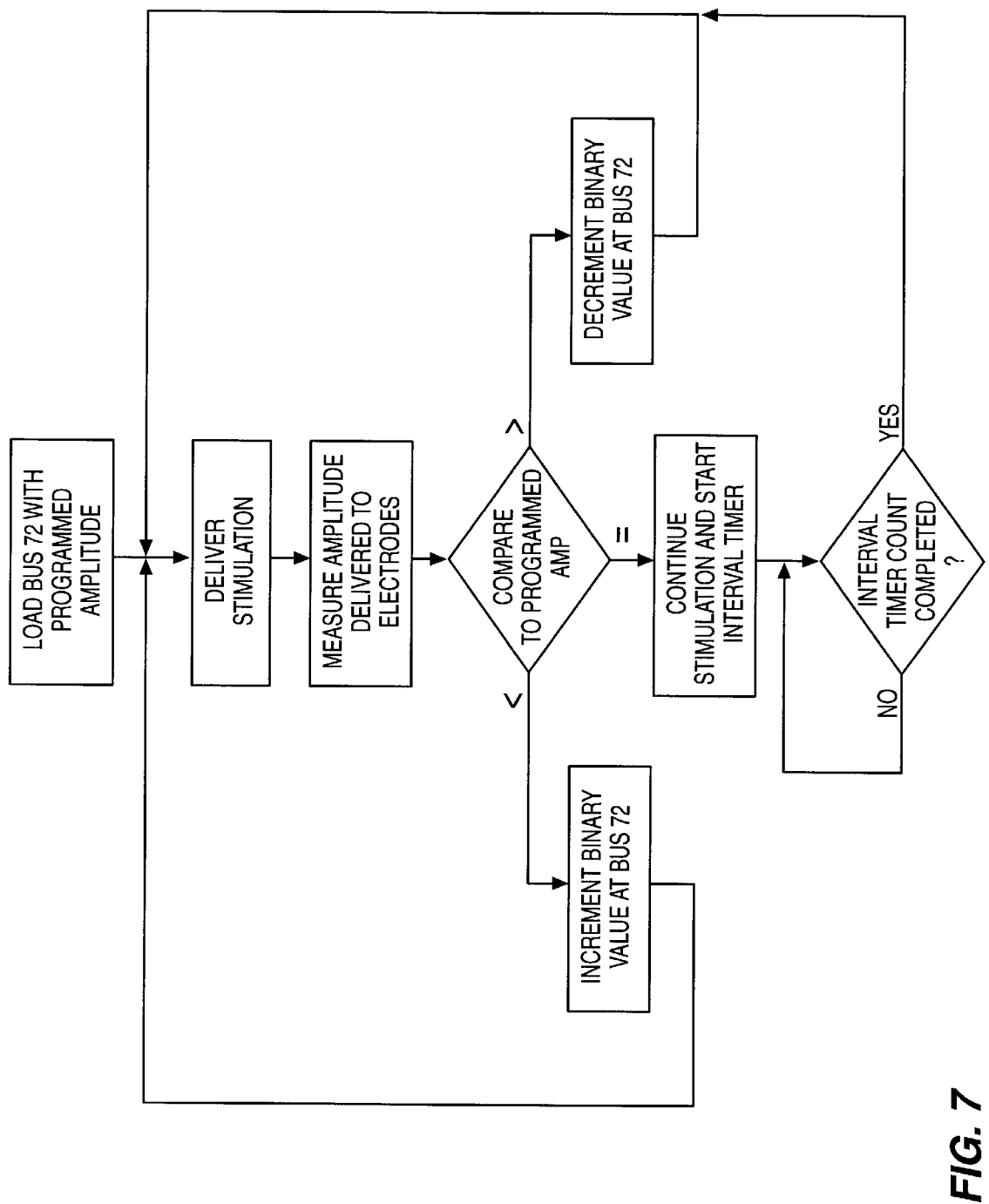
FIG. 7 is a flow chart for a closed loop stimulation routine.

Referring to FIGS. 2 and 7, upon programming a new value for amplitude, pulse width or rate, the "calibration" software routine set forth in FIG. 7 is used to determine the binary value required at the amplitude bus 72 (FIG. 2) for making the amplitude delivered to the electrodes be equal to the programmed amplitude. This routine comprises five steps: (1) Load amplitude bus 72 with the programmed amplitude value, (2) initiate stimulation, (3) measure with A/D port 160 the voltage amplitude "delivered" to the electrodes, (4) compare the measured amplitude with the programmed amplitude, (5) increment or decrement, as required, the value at the amplitude bus 72 until the delivered amplitude equals the programmed amplitude. After this initial adjustment, steps 3, 4 and 5 are repeated periodically, the time interval being controlled by a software interval timer, and the binary value at amplitude bus 72 is readjusted as required to make sure that the delivered amplitude is maintained equal to the programmed amplitude. The time interval between calibrations is a software variable which can be programmed to minutes or hours. This closed-loop stimulation guarantees a regulated, constant pulse amplitude as a function of load, frequency, pulse width, and component aging.

Another unique aspect of the present invention, is the capability of the stimulator 12 to operate each electrode at a different pulse width and rate.

Referring to FIGS. 2 and 3, control logic 42 includes four (4) pulse generating ports: Pulse A, Pulse B, Pulse C and Pulse D for electrodes A, B, C and D, respectively. The pulse width and rate for each port is controlled by an independent software timing loop. Referring to FIG. 4, Pulse A, Pulse B, Pulse C and Pulse D are connected to one input of NAND gates 161–164, respectively. Output enable lines 172, 156, 158, 174 are connected to the other input to NAND gates 171–179, respectively. Therefore, during Pulse A time the negative side of C1 is connected via transistor N6 to electrode A, delivering a stimulus voltage to electrode A having autonomous pulse width and repetition rate. Similarly, during Pulse B time the negative side of C2 is connected via transistor N7 to electrode B, delivering an stimulus voltage to electrode B having autonomous pulse width and repetition rate. Similarly, during Pulse C time the negative side of C3 is connected via transistor N8 to electrode C, delivering an stimulus voltage to electrode C having autonomous pulse width and repetition rate. Similarly, during Pulse D time the negative side of C4 is connected via transistor N9 to electrode D, delivering an stimulus voltage to electrode D having autonomous pulse width and repetition rate.

Another unique aspect of the present invention, is the capability of the tissue stimulator 12 to respond to signals picked up by a biological sensor. The biological sensor could be one of the stimulating electrodes which can also pick-up signals from specific tissue. An example for such application would be for alleviating the tremors of patients suffering from parkinson syndrome. It now well known to neurologists and researchers that Parkinsonian tremors can be alleviated or terminated by electrical stimulation of the thalamus. It is also known that when these patients go to sleep the tremors disappear and, therefore, electrical stimulation is not required. Today, Parkinsonian patients receive electrical thalamic stimulation continuously around the clock, wasting precious battery power when the patient sleeps. The morphology of the brain waves changes significantly when the Parkinsonian patient goes to sleep. By placing an electrode proximal to the appropriate brain cells, changes in brain wave indicating a "sleeping" state can be positively detected and the stimulation can be interrupted until "awake" brain signals are recognized. The problem is that the morphology of brain waves during periods of sleep and awake, often are different from patient to patient, making recognition by conventional means difficult. What is needed is a biological sensor capable of (a) learning the morphology of "sleep" versus "awake" brain waves of a particular patient, (b) to compare on a real-time basis the morphology of the brain waves been received against the learned "sleep" and "awake" brain waves, and (c) respond by interrupting stimulation upon acquiring "sleep" brain waves and resuming stimulation upon acquiring "awake" brain waves.

Referring to FIGS. 2 and 4, the electrode multiplexer 54 is utilized to connect either electrode A, B, C or D to amplifier 56. Bus 80 controls which electrode will be connected to amplifier 56. Control lines within bus 79 are used to, (a) turn on/off amplifier 56, (b) control it's gain, and (c) control it's pass band. The output of amplifier 56 is connected, via line 160, to the A/D port of control logic 42 in FIG. 3. In a clinical setting the physician will enable control logic 42 to learn and record the morphology of "awake" and "sleep" brain waves of the patient. Both morphologies are recorded in non-volatile memory 26 (FIG. 1). Later, in daily use control logic 42 will compare, under software control and at a predetermined intervals, the on-going brains waves against the recorded "awake" and "sleep" waves and will automatically interrupt or resume stimulation as needed.

Another useful clinical application for a biological sensor would be to sense a prerecorded morphology which would cause the tissue stimulator 12 to up-link a command to an implanted infusion pump to deliver a predetermined volume of drug.

Another useful clinical application for a biological sensor would be to recognize the prerecorded morphology of an evoked response resulting from stimulating a remote nerve tissue for the purpose of automatically establishing the stimulation parameters required to provoke paresthesia in a pain patient. For example, electrode A could be used to deliver a stimulus pulse to specific nerve(s) in the spinal column while electrode B is used to detect the evoked response signals which are then compared against a prerecorded morphology. The tissue stimulator 12 periodically will go into a "search" mode, whereby the amplitude is first reset to zero and then it is slowly increased in very small steps until the desired evoked potential is detected indicating that paresthesia has been reestablished.

Another unique aspect of the present invention, is the capability of the tissue stimulator 12 to provide an impedance histogram showing changes in lead impedance as a function of time. This impedance histogram can be useful to the physician to determine if changes in electrode position within the epidural space are occurring. Referring to FIG. 1, micro-controller 20 can, upon receiving a down-linked command or at preselected intervals, direct any I/O module 16 to measure electrode impedance on any of the four channels. Referring to FIG. 2, control logic 42 can initiate upon command by micro-controller 20 (FIG. 1) to measure lead impedance, and the resulting value plus time and date of the measurement can be stored in the non-volatile memory 26 (FIG. 1). Later, the physician can interrogate all these values and a histogram can be printed for physician evaluation. Lead impedance measurement can be programmed to occur either on a regular basis or upon sensing a specific event such as when the patient makes adjustments to any of the stimulation values.

Another unique aspect of the present invention, is the capability of the tissue stimulator 12 to provide means for recording in non-volatile memory the final value of any stimulation parameter after an adjustment is made, along with the time and date when the adjustments were made, in order to later telemeter to an external unit a histogram for each stimulation parameter for evaluation by the physician. Referring to FIG. 1, all parameter adjustments down-linked by an external Patient Programmer device (not shown) are processed by micro-controller 20. The resulting value and the time and date of the adjustment are recorded into the non-volatile memory 26. Later, the Physician can recall these values and times and an "adjustments" histogram can be printed under control of the Physician Programmer unit (not shown).

Another unique aspect of the present invention, is the capability of the stimulator 12 to stimulate with either constant voltage or constant current pulses. Referring to FIGS. 2 and 4, constant voltage stimulation is accomplished by charging the amplitude holding capacitor (C1, C2, C3 or C4) until the amplitude delivered to the electrodes as measured by the A/D port of the control logic 42 is equal to the programmed amplitude. A calibration cycle is periodically repeated to compensate for changes in load, pulse width, rate and aging of components, whereby the measured amplitude is compared to the target amplitude and the charge to the holding capacitor is adjusted until the measured amplitude equals the programmed amplitude. In the constant current stimulation, control logic 42 (a) measures lead impedance as explained earlier, and (b) adjusts the pulse voltage until the programmed current value is delivered using the following conventional formula:

$$\text{Pulse current} = \frac{\text{Pulse voltage}}{\text{lead impedance}}$$

Periodically, lead impedance is measured and pulse voltage is adjusted in order to maintain pulse current constant as a function of changes in lead impedance, rate, pulse width, component aging and temperature.

Another unique aspect of the present invention, is the capability of the stimulator 12 to stimulate in a biological closed-loop, wherein the brain's evoked potential is sensed in response to electrical stimulation of specific remote nerve tissue, and stimulation parameters are slowly increased until the evoked potential is sensed in order to establish the minimum level of stimulation energy capable of evoking the brain's response. Referring to FIGS. 2 and 4, for example, if electrode A is utilized to stimulate a nerve tissue remote from the brain and electrode B is used to sense in the brain the corresponding evoked response potential, logic control 42 can be used to periodically switch to a "paresthesia threshold search" software routine, wherein the stimulation amplitude are slowly increased until the "evoked potential" is sensed. This process can also be repeated for pulse width and rate until stimulation values resulting in minimum power consumption are established. This feature is useful for automatically matching stimulation amplitude to a continuously changing paresthesia threshold, due to posture changes or changes in the medical condition of the patient.

From the foregoing description, it will be apparent that the implantable, modular tissue stimulator and method for using same of the present invention has a number of advantages, some of which have been described above and others of which are inherent in the invention. Also, it will be understood that modifications can be made to the implantable, modular tissue stimulator without departing from the teachings of the present invention. Accordingly, the scope of the invention is only to be limited as necessitated by the accompanying claims.

We claim:

1. An implantable, modular tissue stimulator, comprising: (a) a master controller having a control logic, a memory, means for receiving signals down-linked by external devices representing commands or program data and means for up-linking signals representing stored data or commands to external devices; (b) two or more I/O modules each having two or more stimulating electrodes, means for delivering electrical pulses of different amplitude, pulse width and rate to each electrode, means for powering the circuitry driving each electrode from an isolated power source; and, (c) a bidirectional bus carrying data and controlling signals between said master controller and said I/O modules.

2. The modular tissue stimulator of claim 1, wherein each I/O module includes (a) means for, in between stimulus pulses, switching a capacitor to power supply lines in order to charge said capacitor to the supply voltage, (b) means for, during each stimulus pulse, disconnecting said capacitor from the power supply lines so that, during each stimulus pulse, said capacitor exclusively provides the operating power to the I/O module and whereby said capacitor becomes a power source isolated from other I/O modules.

3. The modular tissue stimulator of claim 1, wherein said I/O module includes means for non-invasively programming the current paths between all stimulating electrodes, wherein each electrode can be designated to (a) exclusively source current to specified target electrode(s) and to exclude all other non-specified electrodes(s), or (b) to source current to all other electrode(s) on a non-exclusive basis.

4. The modular tissue stimulator of claim 1, wherein said I/O module includes one pulse amplitude holding capacitor per electrode, said holding capacitor being charged in between stimulus pulses to the voltage amplitude to be delivered later during the stimulus pulse.

5. The modular tissue stimulator of claim 4, wherein said I/O module includes (a) a programmable DC/DC converter, and (b) means for multiplexing the output of said DC/DC converter to said holding capacitor.

6. The modular tissue stimulator of claim 5, wherein said I/O module includes switching means for alternatively connecting said holding capacitors to either, said multiplexing means during charging of said holding capacitor, or to the designated electrode during delivery of the stimulus pulse.

7. The modular tissue stimulator of claim 6 wherein said I/O module includes (a) analog means for measuring the pulse voltage delivered to said electrodes, (b) means for comparing the measured voltage against a non-invasively programmed value, and (c) means for adjusting the target voltage of said DC/DC converter until the measured pulse voltage equals the programmed value.

8. The modular tissue stimulator of claim 1, wherein said I/O module includes two or more ports for generating pulses, each port being capable of generating pulses having different pulse width and repetition rate than other port(s).

9. The modular tissue stimulator of claim 1, wherein said I/O module includes multiplexing means for selectively switching said electrodes to the input of an amplifier for the purpose of amplifying biological signals picked up by the selected electrode(s).

10. The modular tissue stimulator of claim 9, wherein said I/O module includes (a) means for converting amplified signal into a digital format, and (b) means for recording into said memory the digitally formatted signal.

11. The modular tissue stimulator of claim 9 wherein said I/O module includes (a) means for comparing the morphology of said prerecorded biological signal against the morphology of freshly acquired biological signals, (b) means for triggering a preselected response, i.e., up-linking a specific command or initiating a preselected stimulation protocol, upon a positive comparison between said prerecorded signal and said freshly acquired signal.

12. The modular tissue stimulator of claim 9 wherein each I/O module includes (a) means for sensing brain waves arriving at preselected electrodes, (b) means for, upon receiving an externally down-linked command, initiating recording of the brain waves into said memory while the patient is sleeping, (c) means for comparing the morphology of the prerecorded brain waves against the morphology of freshly acquired brain waves, (d) means for interrupting the delivery of stimulation pulses upon a positive comparison between the prerecorded and freshly acquired brain waves, (e) means for resuming delivery of stimulation pulses upon a negative comparison between the prerecorded and freshly acquired brain waves.

13. The modular tissue stimulator of claim 9 wherein said preselected response is a command up-linked to a medical device, said command causing said medical device to initiate delivery of medical therapy.

14. The modular tissue stimulator of claim 9 wherein each I/O module includes means for up-linking a coded signal to a paging device located external to a human, said paging device being carried by the human body, (b) means for enabling said coded signal to cause said paging device to display specific message, (c) means for enabling said coded signal to cause said paging device to emit an audible sound or to vibrate, (d) means for allowing the human to stop said vibration or audible sound.

15. The modular tissue stimulator of claim 1 wherein said I/O module includes means for measuring electrode impedance, said means comprising (a) a constant current source, (b) means for switching said constant current source to one or more electrodes while a negative voltage is applied to other electrode(s), (c) means for measuring the resulting voltage drop across said constant current source, (d) means for calculating electrode impedance by dividing said constant current value into the voltage drop value.

16. The modular tissue stimulator of claim 1 wherein said I/O module includes (a) means for measuring the electrode impedance, either upon command or at preselected time intervals, (b) means for recording in said memory the impedance value measured along with the time and date when the measurement was made, and (c) means for up-linking all the recorded measurements along with the corresponding times and dates.

17. The modular tissue stimulator of claim 1 wherein said I/O module includes means for generating stimulus pulses having a constant current value comprising (a) means for non-invasively programming the desired stimulation current value, (b) means for measuring the voltage delivered to the electrodes, (c) means for adjusting the pulse voltage delivered to the electrodes, (d) means for measuring electrode impedance, (e) means for dividing the electrode impedance value into the measured pulse voltage value in order to calculate the delivered current value, (f) means for comparing the delivered current value against the programmed current value, (g) means for adjusting the pulse voltage until the delivered current value equals the programmed current, (h) means for periodically repeating steps (a) through (f) and readjusting the pulse voltage as required to maintain the delivered current value equal to the programmed current value.

18. The modular tissue stimulator of claim 1, wherein said I/O module includes (a) means for receiving and decoding down-linked commands to change any one of the stimulation parameters, (b) means for recording in said memory the new parameter values along with the time and date in which the changes were made, and (c) means for up-linking all the recorded values along with corresponding times and dates.

19. The modular tissue stimulator of claim 1, wherein said I/O module includes (a) means for sensing the brain's evoked potential in response to electrical stimulation of specific remote nerve tissue, (b) means for slowly adjusting stimulation parameters until the evoked potential is sensed, and (c) means for periodically repeating steps (a) and (b) in order to (1) establish the stimulation parameters capable of evoking the brain's response with minimum power consumption, and (2) automatically maintain an effective level of therapy without patient or physician intervention.

20. The modular tissue stimulator of claim 1, wherein said I/O module includes (a) means for sensing specific brain waves symptomatic to the onset of an epileptic seizure, and (b) means for initiating a preselected stimulation schedule upon sensing the symptomatic brain waves.

21. The modular tissue stimulator of claim 1, wherein each I/O module includes (a) means for delivering stimulus pulses to two or more channels asynchronously but with a delay between the pulse delivered to a first channel versus the pulse delivered to other channel(s), (b) means for non-invasively programming the delay to a clinical useful value.

22. The modular tissue stimulator of claim 1 wherein said I/O module includes means for non-invasively programming the current paths between all I/O modules and wherein an electrode (s) in one I/O module can be designated to (a) exclusively source current to another specified target electrode(s) in other I/O module(s) and to exclude all other non-specified electrodes in said I/O modules, or (b) to source current to all other electrode(s) in all I/O modules on a non-exclusive basis.

23. An implantable modular tissue stimulator comprising a master controller, a plurality of I/O modules and a bi-directional bus coupled between said master controller and said I/O modules; said master controller including control logic means, memory means, coupled to said control logic means, coupled to said control logic for receiving signals downlinked from an external device, said signals representing data or commands, and means, coupled to said control logic for uplinking signals to one or more external devices, said uplinking signals representing stored data or commands to said external devices; each I/O module having at least two stimulating electrodes coupled thereto, circuit means in said module for delivering electrical pulses to said stimulating electrodes, each pulse being capable of having a different amplitude, pulse width and frequency or rate of repetition, and power means for supplying power to each circuit means from an isolated power source.

24. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source each stimulation channel and each stimulation channel including (d) first switching means for, in between stimulus pulses, switching a capacitor to the power supply lines in order to change said capacitor to the supply voltage, and (e) second switching means for, during each stimulus pulse, disconnecting said capacitor from the power supply lines so that, during each stimulus pulse, said capacitor exclusively provides the operating power to said driving circuitry and whereby said capacitor becomes a power source isolated from other channels.

25. The multichannel tissue stimulator of claim 24, wherein each channel includes (a) a programmable DC/DC converter, and (b) means for connecting the output of said DC/DC converter, to said holding capacitor.

26. The multichannel tissue stimulator of claim 25, wherein each channel includes switching means for alternatively connecting said holding capacitors to either, said DC/DC converter during charging of said holding capacitor, or to the designated electrode during delivery of the stimulus pulse.

27. The multichannel tissue stimulator of claim 25, wherein each channel includes (a) means for measuring the pulse voltage delivered to said electrodes, (b) means for comparing the measured voltage against a non-invasively programmed value, (c) means for adjusting the target voltage of said DC/DC converter until the measured pulse voltage equals the programmed value.

28. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and including means for non-invasively programming the current paths between all stimulating channels and providing means whereby each channel can be designated to (a) exclusively source current to specified target channel(s) and to exclude all other non-specified channel(s), or (b) to source current to all other channel(s) in a non-exclusive basis.

29. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and each channel including one pulse amplitude holding capacitor, and said holding capacitor being charged in between stimulus pulses to the voltage amplitude to be delivered later during the stimulus pulse.

30. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and at least one channel including means for switching said channel to the input of an amplifier for the purpose of amplifying biological signals picked up by the electrode connected to said channel.

31. The multichannel tissue stimulator of claim 30, wherein at least one channel includes (a) means for converting the amplified signal into a digital format, and (b) means for recording into memory the digitally formatted signal.

32. The multichannel tissue stimulator of claim 30, wherein at least one channel includes (a) means for comparing the morphology of the prerecorded biological signal against the morphology of freshly acquired biological signals, (b) means for triggering a preselected response, i.e., up-linking a specific command or initiating a preselected stimulation protocol, upon a positive comparison between the prerecorded signal and the freshly acquired signal.

33. The multichannel tissue stimulator of claim 32, wherein the preselected response is a command up-linked to a medical device, said command causing aid medical device to initiate delivery of medical therapy.

34. The multichannel tissue stimulator of claim 30, wherein at least one channel includes (a) means for sensing brain waves arriving at preselected electrodes, (b) means for, upon receiving an externally down-linked command, initiate recording of the brain waves into a memory while the patient is sleeping, (c) means for comparing the morphology of the prerecorded brain waves against the morphology of freshly acquired brain waves, (d) means for interrupting the delivery of stimulation pulses upon a positive comprising between the prerecorded and freshly acquired brain waves, (e) means for resuming delivery of stimulation pulses upon a negative comparison between the prerecorded and freshly acquired brain waves.

35. The multichannel tissue stimulator of claim 30, wherein means are included for (a) up-linking a coded signal to a paging device located external to a human, said paging device being carried by the human, (a) said coded signal causing said paging device to display a specific message, (c) means for enabling said coded signal to cause said paging device to emit an audible sound or to vibrate, (d) allowing the human to stop the vibration or audible sound.

36. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and each channel including means for measuring electrode impedance comprising (a) a constant current source, (b) means for switching said constant current source to one or more electrodes while a negative voltage is applied to other electrode(s), (c) means for measuring the resulting voltage drop across said constant current source, and (d) means for calculating electrode impedance by dividing the constant current value into the voltage drop value.

37. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source, memory means, and each channel including (a) means for measuring said electrode impedance, either upon command or at preselected time intervals, (b) means for recording in said memory means the impedance value along with the time and date when the measurement was made, and (c) means for up-linking all the recorded measurement along with the corresponding times and dates.

38. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and at least one channel including means for generating stimulus pulses having a constant current value comprising (a) means for non-invasively programming the desired stimulation current value, (b) means for measuring the voltage delivered to the electrodes, (c) means for adjusting the pulse voltage delivered to the electrodes, (d) means for measuring electrode impedance, (e) means for dividing the electrode impedance value into the measured pulse voltage value in order to calculate the delivered current value, (f) means for comparing the delivered current value against the programmed current value, (g) means for adjusting the pulse voltage until the delivered current value equals the programmed current, (h) means for periodically repeating steps (a) through (f) and readjusting the pulse voltage as required to maintain the delivered current value equal to the programmed current value.

39. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and including means for (a) receiving and decoding down-linked commands to change any one of the stimulation parameters, for recording in said memory the new parameter values along with the time and date in which the changes were made, and (b) means for up-linking all the recorded values along with corresponding times and dates.

40. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and each channel including (a) means for sensing the brain's evoked potential in response to electrical stimulation of specific remote nerve tissue, (b) means for slowly adjusting stimulation parameters until the evoked potential is sensed, and (c) means for periodically repeating steps (a) and (b) in order to (1) establish the stimulation parameters capable of evoking the brain's response with minimum power consumption, and (2) automatically maintain an effective level of therapy without patient or physician intervention.

41. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and at least one channel including (a) means for sensing specific brain waves symptomatic to the onset of an epileptic seizure, and (b) means for initiating a preselected stimulation schedule upon sensing said symptomatic brain waves.

42. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and including means for (a) delivering stimulus pulses to two or more channels asynchronously but with a delay between the pulse delivered to a first channel versus the pulse delivered to other channel(s) and (b) non-invasively programming the delay to a clinical useful value.

43. An implantable, multichannel tissue stimulator having two or more channels of stimulation each being connected to an implantable electrode and each channel including (a) means for delivering electrical pulses of different amplitude, different pulse width and different repetition rate to each channel, (b) circuitry for driving each electrode, and (c) means for powering the circuitry driving each electrode from an isolated power source and each stimulation channel including means for non-invasively programming the current paths between all channels and wherein an electrode(s) in one channel can be designated to (a) exclusively source current to another specified target electrode(s) in other channels and to exclude all other non-specified electrodes in said channels, or (b) to source current to all other electrode (s) in all channels on a non-exclusive basis.

44. An implantable multichannel tissue stimulator comprising a control logic and a plurality of channels; said control logic including memory means coupled to said control logic, means, coupled to said control logic, for receiving signals downlinked from an external device, said signals representing data or commands, and means, coupled to said control logic, for uplinking signals to one or more external devices, said up-linked signals representing stored data or commands to said external devices; each stimulating channel having at least two stimulating electrodes coupled thereto, circuit means in said module for delivering electrical pulses to said stimulating electrodes, each pulse being capable of having different amplitude, pulse width and frequency or rate of repetition, and power means for supplying power to each circuit means from an isolated power source.

* * * * *

UNITED STATES PATENT AND TRADEMARK OFFICE
CERTIFICATE OF CORRECTION

PATENT NO.    : 5,941,906
DATED         : August 24, 1999
INVENTOR(S)   : Francisco J. Barreras, Sr., Roberto Echarri and Guillermo Echarri It is certified that error appears in the above-identified patent and that said Letters Patent is hereby corrected as shown below:

Column 8,
Line 25, "NS" should be -- N5 --;

Column 9,
Line 2, "were" should be -- where --;

Column 11,
Lines 35, 39 and 42, "an" should be -- a --;
Line 51, "parkinson" should be -- Parkinson's --;
Line 51, after "it", insert -- is --;

Column 12,
Line 4, delete "been";
Line 21, delete "a";

Column 18,
Line 4, "aid" should be -- said --;
Line 21, after human "a" should be -- b --.

Signed and Sealed this

Sixteenth Day of July, 2002

Attest:

JAMES E. ROGAN
Attesting Officer     Director of the United States Patent and Trademark Office